United States Patent
Gavenda et al.

(10) Patent No.: US 8,217,061 B2
(45) Date of Patent: Jul. 10, 2012

(54) POLYMORPHS OF SORAFENIB TOSYLATE AND SORAFENIB HEMI-TOSYLATE, AND PROCESSES FOR PREPARATION THEREOF

(75) Inventors: Aleš Gavenda, Ostrava-Lhotka (CZ); Alexandr Jegorov, Dobrá Voda (CZ); Pierluigi Rossetto, Lodi (IT); Peter Lindsay MacDonald, Gentilino (CZ); Augusto Canavesi, Locate Varesino (IT)

(73) Assignee: Sicor Inc., Irvine, CA (US)

( * ) Notice: Subject to any disclaimer, the term of this patent is extended or adjusted under 35 U.S.C. 154(b) by 620 days.

(21) Appl. No.: 12/356,004

(22) Filed: Jan. 19, 2009

(65) Prior Publication Data

US 2009/0192200 A1    Jul. 30, 2009

Related U.S. Application Data

(60) Provisional application No. 61/011,630, filed on Jan. 17, 2008, provisional application No. 61/131,033, filed on Jun. 4, 2008, provisional application No. 61/082,723, filed on Jul. 22, 2008.

(51) Int. Cl.
*A61K 31/44* (2006.01)
*C07D 213/81* (2006.01)

(52) U.S. Cl. ..................... 514/350; 546/298

(58) Field of Classification Search .................. None
See application file for complete search history.

(56) References Cited

FOREIGN PATENT DOCUMENTS

| | | |
|---|---|---|
| WO | WO-00/41698 A1 | 7/2000 |
| WO | WO-00/42012 A1 | 7/2000 |
| WO | WO-2006/034796 A1 | 4/2006 |
| WO | WO-2006/034797 A1 | 4/2006 |

*Primary Examiner* — Zinna Northington Davis
(74) *Attorney, Agent, or Firm* — Kenyon & Kenyon LLP

(57) ABSTRACT

Provided are sorafenib hemi-tosylate, polymorphs thereof, polymorphs of sorafenib tosylate, preparation thereof and pharmaceutical compositions thereof.

13 Claims, 6 Drawing Sheets

POLYMORPHS OF SORAFENIB TOSYLATE AND SORAFENIB HEMI-TOSYLATE, AND PROCESSES FOR PREPARATION THEREOF

CROSS REFERENCE TO RELATED APPLICATIONS

The present invention claims the benefit of the following U.S. Provisional Patent Application Nos. 61/011,630, filed Jan. 17, 2008; 61/131,033, filed Jun. 4, 2008; and 61/082,723, filed Jul. 22, 2008. The contents of these applications are incorporated herein by reference.

FIELD OF THE INVENTION

The present invention relates to sorafenib hemi-tosylate, polymorphs thereof, polymorphs of sorafenib tosylate, preparation thereof and pharmaceutical compositions thereof.

BACKGROUND OF THE INVENTION

Sorafenib tosylate, 4-(4-{3-[4-chloro-3-(trifluoromethyl)phenyl]ureido}phenoxy)-N2-methylpyridine-2-carboxamide 4-methylbenzenesulfonate of the following formula

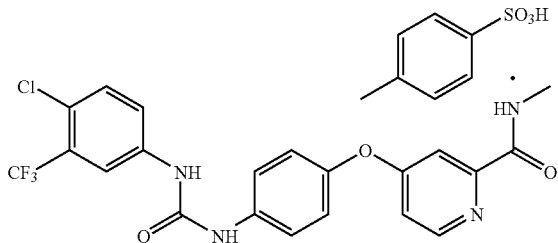

is marketed as Nexavar® by Bayer for treatment of advanced renal cell carcinoma (primary kidney cancer). It has also received "Fast Track" designation by the FDA for the treatment of advanced hepatocellular carcinoma (primary liver cancer).

Sorafenib and its salts, such as the tosylate salt and a process for preparation thereof are disclosed in WO 00/41698 A1.

WO 00/042012 A1 describes sorafenib base, pharmaceutically acceptable salts and their use.

WO 06/034796 A1 discloses processes for preparing sorafenib base and its tosylate salt.

WO 06/034797 reports crystalline forms of sorafenib tosylate, forms I, II, and III, methanol solvate, ethanol solvate and preparation thereof. Crystalline Sorafenib tosylate form III is characterized by a PXRD pattern having peaks selected from a list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2theta. Crystalline Sorafenib tosylate methanol solvate is characterized by a PXRD pattern having peaks selected from a list consisting of: 8.0, 8.4, 9.3, 11.2, 12.2, 13.0, 13.4, 15.8, 16.3, 16.9, 17.7, 18.3, 18.7, 19.0, 19.4, 20.2, 20.5, 20.9, 21.4, 21.7, 22.3, 22.4, 23.8, 24.0, 24.4, 24.7, 24.9, 25.2, 25.7, 26.0, 26.1, 26.4, 26.9, 27.0, 27.5, 27.7, 28.1, 28.3, 28.8, 29.1, 29.7, 30.2, 30.4, 30.7, 30.8, 31.4, 31.6, 31.9, 32.3, 32.6, 32.9, 33.4, 33.8, 34.0, 34.2, 34.5, 34.9, 36.2, 36.6, 37.2, and 37.7±0.2 degrees 2theta. Crystalline Sorafenib tosylate ethanol solvate is characterized by a PXRD pattern having peaks selected from a list consisting of: 7.9, 8.4, 9.3, 9.5, 11.2, 12.0, 12.2, 12.8, 13.4, 15.9, 16.1, 16.8, 17.4, 17.7, 18.1, 18.3, 18.6, 18.8, 19.4, 20.0, 20.4, 21.0, 21.2, 21.5, 21.7, 22.3, 22.4, 22.8, 23.3, 23.6, 23.8, 24.3, 24.7, 25.3, 25.8, 25.9, 26.4, 26.9, 27.3, 27.6, 28.3, 28.8, 29.1, 29.5, 29.7, 30.2, 30.4, 30.9, 31.4, 32.0, 32.6, 32.9, 33.2, 33.7, 33.9, 34.5, 35.5, 36.0, 36.3, 36.6, 37.1, and 37.7±0.2 degrees 2theta.

The present invention discloses sorafenib hemi-tosylate, polymorphs of sorafenib hemi-tosylate and polymorphs of sorafenib tosylate, and processes for preparation thereof.

Polymorphism, the occurrence of different crystal forms, is a property of some molecules and molecular complexes. A single compound, like sorafenib hemi-tosylate or sorafenib tosylate, may give rise to a variety of crystalline forms having distinct crystal structures and physical properties like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Therefore, there is a need for additional crystalline forms of sorafenib hemi-tosylate or sorafenib tosylate.

SUMMARY OF THE INVENTION

In one embodiment, the invention encompasses a process for preparing crystalline Sorafenib tosylate characterized by a PXRD pattern having the peaks selected from the list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2theta; comprising a) providing a suspension comprising Sorafenib tosylate, p-toluenesulfonic acid ("PTSA") and a solvent selected from a group consisting of methanol, a mixture of methanol and NMP, a mixture of methanol and DMSO and a mixture thereof to obtain Sorafenib tosylate methanol solvate, and b)

drying Sorafenib tosylate methanol solvate at a temperature greater than room temperature.

In one embodiment, the invention encompasses a process for preparing crystalline Sorafenib tosylate methanol solvate characterized by a PXRD pattern having the peaks selected from the list consisting of: 8.0, 8.4, 9.3, 11.2, 12.2, 13.0, 13.4, 15.8, 16.3, 16.9, 17.7, 18.3, 18.7, 19.0, 19.4, 20.2, 20.5, 20.9, 21.4, 21.7, 22.3, 22.4, 23.8, 24.0, 24.4, 24.7, 24.9, 25.2, 25.7, 26.0, 26.1, 26.4, 26.9, 27.0, 27.5, 27.7, 28.1, 28.3, 28.8, 29.1, 29.7, 30.2, 30.4, 30.7, 30.8, 31.4, 31.6, 31.9, 32.3, 32.6, 32.9, 33.4, 33.8, 34.0, 34.2, 34.5, 34.9, 36.2, 36.6, 37.2, and 37.7±0.2 degrees 2theta; comprising providing a suspension comprising Sorafenib tosylate, PTSA and a solvent selected from a group consisting of methanol, a mixture of methanol and NMP, a mixture of methanol and DMSO and a mixture thereof.

In yet another embodiment, the invention encompasses a process for preparing crystalline Sorafenib tosylate ethanol solvate characterized by a PXRD pattern having the peaks selected from the list consisting of: 7.9, 8.4, 9.3, 9.5, 11.2, 12.0, 12.2, 12.8, 13.4, 15.9, 16.1, 16.8, 17.4, 17.7, 18.1, 18.3, 18.6, 18.8, 19.4, 20.0, 20.4, 21.0, 21.2, 21.5, 21.7, 22.3, 22.4, 22.8, 23.3, 23.6, 23.8, 24.3, 24.7, 25.3, 25.8, 25.9, 26.4, 26.9, 27.3, 27.6, 28.3, 28.8, 29.1, 29.5, 29.7, 30.2, 30.4, 30.9, 31.4, 32.0, 32.6, 32.9, 33.2, 33.7, 33.9, 34.5, 35.5, 36.0, 36.3, 36.6, 37.1, and 37.7±0.2 degrees 2theta; comprising suspending crystalline sorafenib tosylate characterized by a PXRD pattern having the peaks selected from the list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2theta in ethanol.

DETAILED DESCRIPTION OF THE INVENTION

Figure 1:
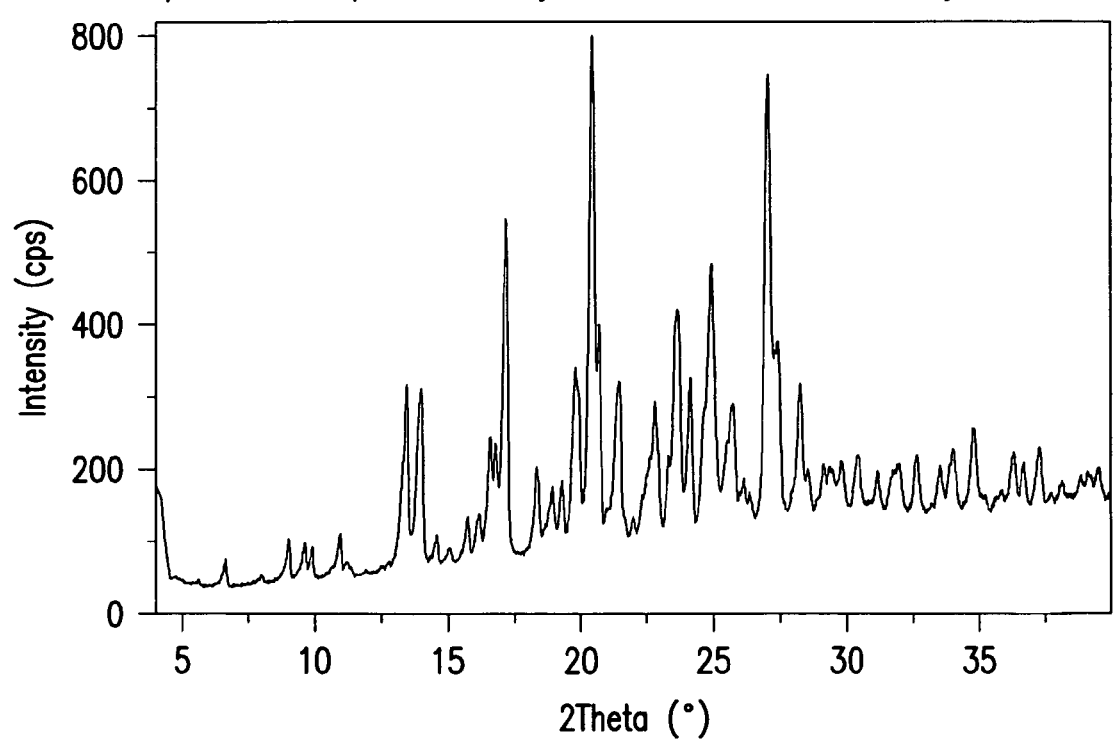
FIG. 1 shows a powder XRD pattern of crystalline Sorafenib hemi-tosylate Form A.

The present invention relates to sorafenib hemi-tosylate, polymorphs of sorafenib hemi-tosylate, polymorphs of sorafenib tosylate, preparation thereof and pharmaceutical compositions thereof.

As used herein, the term "Sorafenib tosylate form III" refers to crystalline Sorafenib tosylate characterized by a PXRD pattern having peaks selected from a list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2theta.

As used herein, the term "Sorafenib tosylate methanol solvate" refers to crystalline Sorafenib tosylate characterized by a PXRD pattern having peals selected from a list consisting of: 8.0, 8.4, 9.3, 11.2, 12.2, 13.0, 13.4, 15.8, 16.3, 16.9, 17.7, 18.3, 18.7, 19.0, 19.4, 20.2, 20.5, 20.9, 21.4, 21.7, 22.3, 22.4, 23.8, 24.0, 24.4, 24.7, 24.9, 25.2, 25.7, 26.0, 26.1, 26.4, 26.9, 27.0, 27.5, 27.7, 28.1, 28.3, 28.8, 29.1, 29.7, 30.2, 30.4, 30.7, 30.8, 31.4, 31.6, 31.9, 32.3, 32.6, 32.9, 33.4, 33.8, 34.0, 34.2, 34.5, 34.9, 36.2, 36.6, 37.2, and 37.7±0.2 degrees 2theta.

As used herein, the term "Sorafenib tosylate ethanol solvate" refers to crystalline Sorafenib tosylate characterized by a PXRD pattern having peaks selected from a list consisting of: 7.9, 8.4, 9.3, 9.5, 11.2, 12.0, 12.2, 12.8, 13.4, 15.9, 16.1, 16.8, 17.4, 17.7, 18.1, 18.3, 18.6, 18.8, 19.4, 20.0, 20.4, 21.0, 21.2, 21.5, 21.7, 22.3, 22.4, 22.8, 23.3, 23.6, 23.8, 24.3, 24.7, 25.3, 25.8, 25.9, 26.4, 26.9, 27.3, 27.6, 28.3, 28.8, 29.1, 29.5, 29.7, 30.2, 30.4, 30.9, 31.4, 32.0, 32.6, 32.9, 33.2, 33.7, 33.9, 34.5, 35.5, 36.0, 36.3, 36.6, 37.1, and 37.7±0.2 degrees 2theta.

As used herein, the term "Overnight" refers to a period of between about 11 and about 18 hours, more preferably 12 hours to about 18 hours, most preferably about 15 hours.

As used herein, the term "room temperature" refers to a temperature between about 20° C. and about 30° C., preferably about 20° C. to about 25° C.

The present invention provides a process for preparing Sorafenib tosylate form III not via Sorafenib tosylate form II, but via a methanol solvate. As reported in WO 2006/034797, page 2, lines 5-7, form II is a meta stable form. Thus, it would be difficult to obtain and maintain this form, and therefore control its conversion to form III.

The process comprises a) providing a suspension comprising Sorafenib tosylate, p-toluenesulfonic acid ("PTSA") and a solvent selected from a group consisting of methanol, a mixture of methanol and NMP, a mixture of methanol and DMSO and a mixture thereof, to obtain Sorafenib tosylate methanol solvate, and b) drying Sorafenib tosylate methanol solvate at a temperature greater than room temperature.

In another embodiment, the invention encompasses a process for preparing crystalline Sorafenib tosylate methanol solvate comprising providing a suspension comprising Sorafenib tosylate, PTSA and a solvent selected from the group consisting of methanol, a mixture of methanol and NMP, a mixture of methanol and DMSO, and mixtures thereof.

Preferably, the suspension is obtained by combining Sorafenib base or Sorafenib tosylate and PTSA in a solvent selected from the group consisting of: methanol, mixtures of methanol and NMP, mixtures of DMSO and methanol, and mixtures thereof, to obtain Sorafenib tosylate methanol solvate, which then precipitates. Preferably, sorafenib base reacts with PTSA providing sorafenib tosylate and residual non reacted PTSA, i.e., the suspension comprising of Sorafenib tosylate methanol solvate contains also residual PTSA. In addition, the suspension comprising of Sorafenib tosylate methanol solvate, which was obtained form sorafenib tosylate as a starting material, also contains residual PTSA. For example, residual PTSA can be between about 20% to about 50% w/w of the starting sorafenib base/tosylate.

When the solvent is methanol, preferably, a methanolic solution of PTSA reacts with a suspension of sorafenib base in methanol. Preferably, the reaction is done at a temperature of about 15° C. to about 30° C., More preferably 20° to about 25° C.

Optionally, the reaction can be done at reflux temperature thus providing a solution comprising sorafenib tosylate, which is then, cooled providing a suspension. Preferably, the cooling is to a temperature of about 15° C. to about 40° C., more preferably 20° to about 30° C.

When the solvent is a mixture of methanol and NMP, preferably, a methanolic solution of PTSA reacts with a suspension of sorafenib base in NMP, providing a solution comprising sorafenib tosylate. Preferably, the reaction is done at about room temperature. Preferably, the solution is then combined with methanol providing a suspension comprising crystalline sorafenib tosylate methanol solvate.

When the solvent is a mixture of methanol and DMSO, preferably PTSA (without a solvent) is combined with a solution comprising Sorafenib tosylate in a mixture of DMSO and methanol, to obtain a second solution. Preferably, the second solution is then combined with an additional amount of methanol and cooled down, providing a suspension comprising Sorafenib tosylate methanol solvate.

The obtained crystalline methanol solvate can then be recovered from the suspension. The recovery excludes drying by heating to a temperature above room temperature, thus avoiding the transformation of the methanol solvate to Sorafenib tosylate form III. Preferably, the recovery is done by filtering and drying at a temperature of about 15° C. to about 30° C., more preferably 20° C. to about 25° C.

Typically, the suspension can be further cooled or maintained to increase the yield of the precipitated crystalline form. Preferably, cooling is to a temperature of about −5° C. to about 10° C., more preferably 5° C. to about 2° C. The suspension can be maintained for a period of about 0.5 hour to about 3 hours, more preferably 1 hour to about 2 hours.

Preferably, the drying in step (b) is done at a temperature of about 80° C. to about 90° C. Preferably, the drying is done for a period of about 10 hours to about 24 hours, more preferably about 14 hours to about 18 hours. Most preferably, the drying is done for a period of about 16 hours. Preferably, the drying is done under vacuum, preferably at a pressure of about 100 mBar.

In yet another embodiment, the invention encompasses a process for preparing crystalline Sorafenib tosylate ethanol solvate comprising suspending sorafenib tosylate form III in ethanol.

Preferably, form III is suspended at a temperature of about 15° C. to about 30° C., more preferably about 20° C. to about 25° C. Preferably, form III is suspended for a period of about 40 hours to about 72 hours, more preferably 45 hours to about 50 hours; during this time Sorafenib tosylate ethanol solvate is expected to be formed.

The process for preparing the said crystalline sorafenib tosylate ethanol solvate may further comprise recovering the crystalline Sorafenib tosylate ethanol solvate from the suspension, however, excluding drying by heating to a temperature above room temperature. The recovery may be done for example by a process comprising filtering the suspension, washing, and drying. Preferably, drying is done at about room temperature, preferably, for a period of about 10 hours to about 24 hours, more preferably 14 hours to about 18 hours. Most preferably, drying is done for a period of about 16 hours.

In one embodiment, the invention encompasses Sorafenib hemi-tosylate.

In another embodiment, the above Sorafenib hemi-tosylate is provided in an isolated form. Preferably, the isolated Sorafenib hemi-tosylate is solid, more preferably, it is crystalline.

As used herein, the term "isolated" in reference to Sorafenib hemi-tosylate corresponds to Sorafenib hemi-tosylate that is physically separated from the reaction mixture.

For example, the separation can be done by precipitation and filtration. More preferably the Sorafenib hemi-tosylate is separated from Sorafenib tosylate providing a composition of Sorafenib hemi-tosylate containing less than about 15% by weight of sorafenib tosylate, more preferably, less than about 10% by weight of sorafenib tosylate, most preferably, less than about 1% by weight of sorafenib tosylate, as measured by titration.

Figure 4:
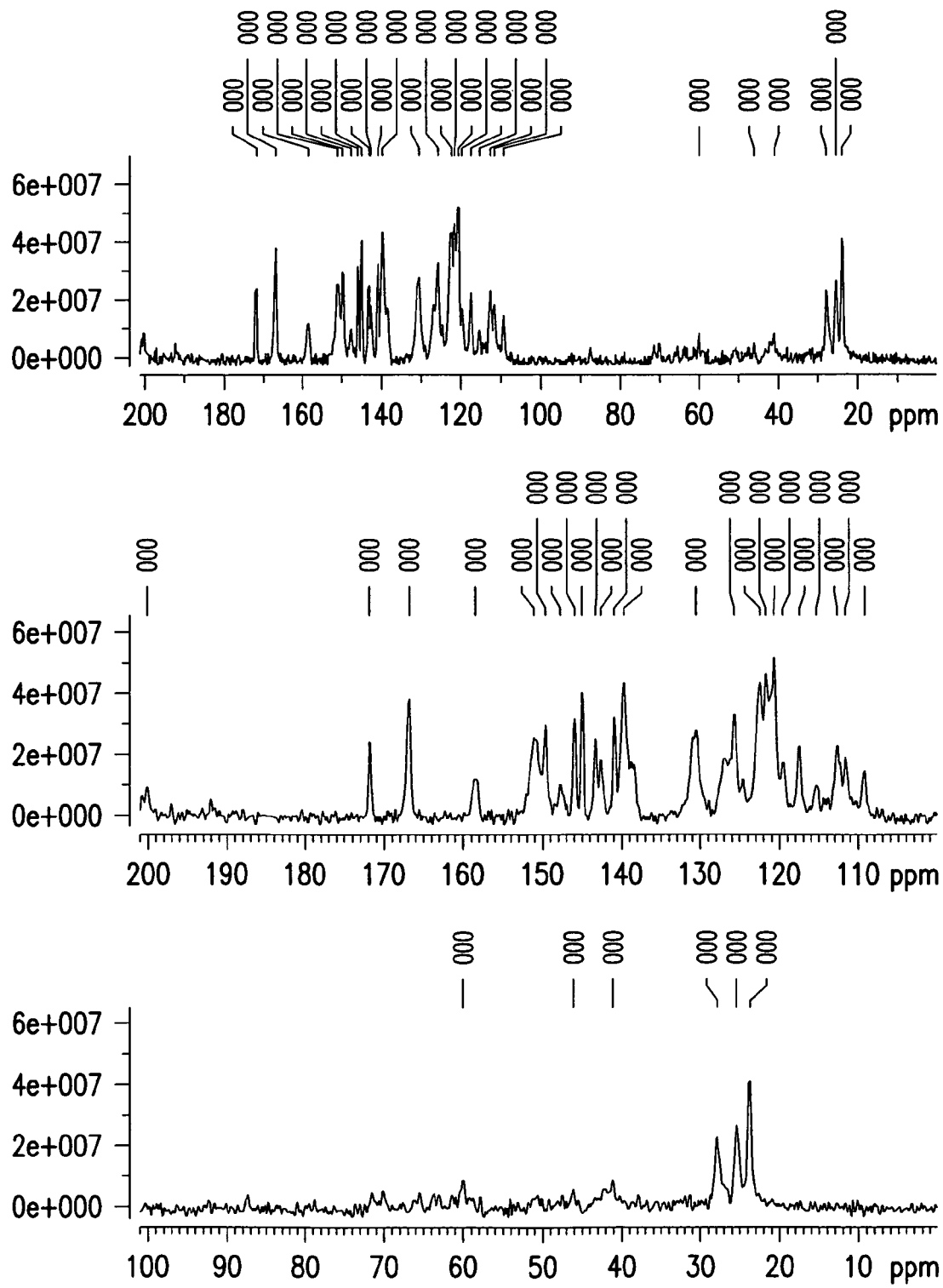
FIG. 4 shows a solid-state NMR spectrum of crystalline Sorafenib hemi-tosylate Form A.
Figure 5:
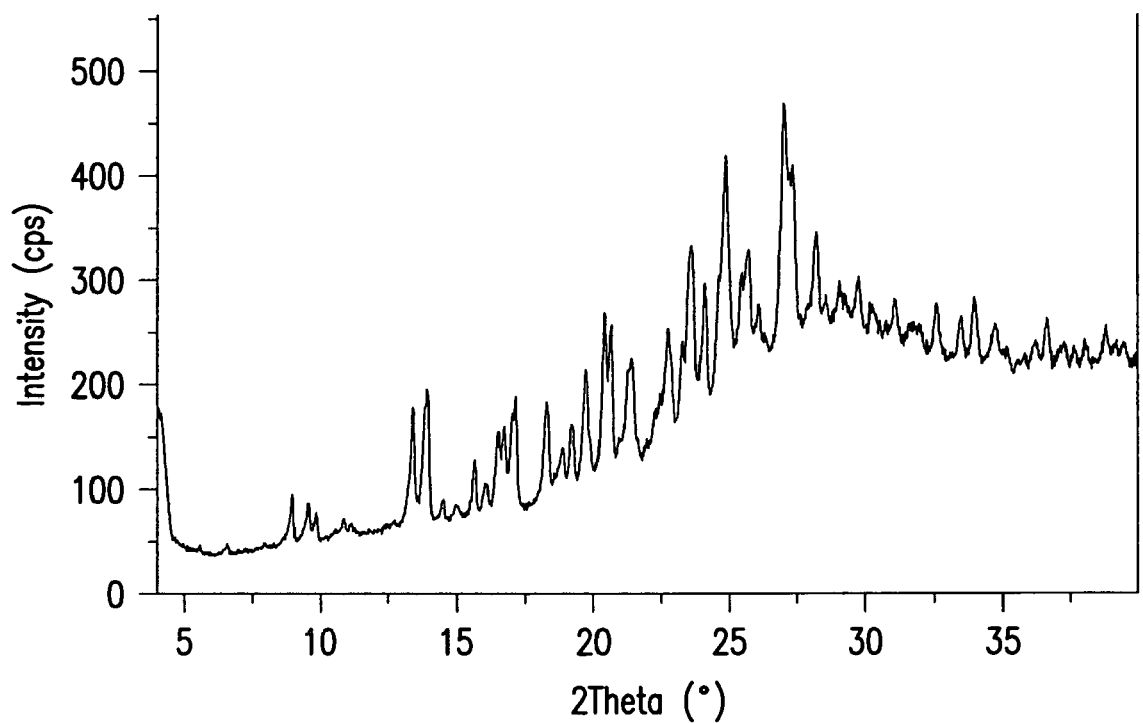
FIG. 5 shows a powder XRD pattern of crystalline Sorafenib hemi-tosylate Form A.

In another embodiment, the invention encompasses crystalline Sorafenib hemi-tosylate characterized by data selected from the group consisting of: a PXRD pattern having any 5 peaks selected from the list consisting of: 6.6, 9.0, 9.6, 13.4, 14.0, 17.2, 18.3, 20.4, 22.8, 24.9 and 27.1±0.2 degrees 2theta; a solid-state 13C NMR spectrum with peaks at about 166.9, 149.7, 119.6, 117.5, 115.4 and 109.3±0.2 ppm; a solid-state 13C NMR spectrum having chemical shifts differences between the signal exhibiting the lowest chemical shift and another in the chemical shift range of 100 to 180 ppm of about 57.6, 40.4, 10.3 and 8.2±0.1 ppm; a PXRD pattern as depicted in FIG. 1, a solid-state $^{13}$C NMR spectrum as depicted in FIG. 4, and combinations thereof. This form is designated form A.

Typically, the signal exhibiting the lowest chemical shift in the chemical shift range of 100 to 180 ppm is at about 109.3±1 ppm.

Preferably, crystalline Sorafenib hemi-tosylate form A is characterized by a PXRD pattern having 3 peaks at about 14.0, 17.2 and 24.9±0.2 degrees 2theta and 2 to 3 peaks selected from the list consisting of: 6.6, 9.0, 13.4, 18.3, 20.4, 23.7 and 27.1±0.2 degrees 2theta.

Crystalline form A of sorafenib hemi-tosylate may be further characterized by data selected from the group consisting of: a PXRD pattern having peaks at about: 9.0, 9.6, 13.4, 14.0, and 17.2±0.2 degrees 2-theta; a PXRD pattern having peals at about: 9.0, 14.0, 18.3, 20.4, and 27.1±0.2 degrees 2-theta; a PXRD pattern having peaks at about: 6.6, 9.0, 14.0, 18.3, and 27.1±0.2 degrees 2-theta; and a PXRD pattern having peaks at about: 6.6, 14.0, 17.2, 20.4, and 24.9±0.2 degrees 2-theta.

In addition, crystalline Sorafenib hemi-tosylate Form A has less than about 15% by weight, preferably, less than about 10% by weight, more preferably, less than about 5% by weight of a Sorafenib tosylate selected from the group consisting of: Sorafenib tosylate Polymorph I, Polymorph II, Polymorph III, methanol solvate and ethanol solvate. Typically, the amount of polymorph I in form A is measured by PXRD using any peak from the following list of peaks at about: 4.4, 14.8 and 17.9 deg±0.2 degrees 2-theta. Typically, the amount of polymorph II in form A is measured by PXRD using any peak from the following list of peaks at about: 7.3, 8.8, 10.5 and 17.6 deg±0.2 degrees 2-theta. Typically, the amount of polymorph III in form A is measured by PXRD using any peak from the following list of peaks at about: 12.0, 17.8 and 21.6 deg±0.2 degrees 2-theta. Typically, the amount of methanol solvate in form A is measured by PXRD using any peak from the following list of peaks at about: 8.4, 9.3, 12.2 and 15.9 deg±0.2 degrees 2-theta. Typically, the amount of ethanol solvate in form A is measured by PXRD using any peak from the following list of peaks at about: 8.4, 12.0, 15.8 and 28.8 deg±0.2 degrees 2-theta.

Sorafenib hemi-tosylate Form A is a stable crystalline form in water suspensions at a temperature of about 20° C., making it ideal for use in the preparation of a dosage form, particularly when the process of wet granulation is used.

As used herein, the term "stable" in reference to Sorafenib hemi-tosylate Form A corresponds to Sorafenib hemi-tosylate which does not undergo hydrolysis of the PTSA moiety in water at a temperature of about 20° C. for a period of at least about 48 hours, preferably, for about 48 hours.

The above form A can be prepared by a process comprising suspending crystalline Sorafenib tosylate form III in water.

Preferably, the suspension is provided by combining sorafenib tosylate form III and water. The suspension is then sonicated in an ultrasound bath. Preferably, the suspension is kept in an ultrasound bath for a period of about 30 minutes to about 10 hours, more preferably for a period of about 1 hour, during this time form A is formed.

Typically, the above suspension is cooled to increase the yield of the precipitated crystalline form. Preferably, the suspension is cooled to a temperature of about 0.5° C. Preferably, the cooling is done with stirring. Preferably, the cooling is performed for a period of about overnight.

The process to prepare crystalline form A can further comprise recovering the crystalline form from the suspension, however, excluding drying by heating to a temperature greater than 100° C. The recovery can be done for example, by filtering, washing and drying. Preferably, the drying is done at a temperature of about 20° C. to about 100° C. Preferably drying is done to a period of about 30 minutes to about 5 hours.

Crystalline form A of sorafenib hemi-tosylate can also be prepared by a process comprising crystallizing Sorafenib hemi-tosylate from acetone 2-propanol, 1-propanol or from mixtures thereof.

Typically, the crystallization comprises providing a solution of Sorafenib hemi-tosylate in acetone 2-propanol, 1-propanol or in mixtures thereof and precipitating the crystalline form to obtain a suspension.

First, sorafenib base is dissolved in the solvent providing a first solution. Preferably, dissolution is at a temperature of about 20° C. to about 82° C., more preferably at a temperature of about 40° C. to about 50° C.

Usually, the first solution is cooled prior to the addition of para-toluene sulfonic acid ("PTSA"). Preferably, the solution is cooled to a temperature of about 0° C. to about 30° C., more preferably at a temperature of about 25° C.

PTSA can be added neat, i.e., without being dissolved in a solvent, or in a solution in water. Preferably, PTSA is added in a form of aqueous solution.

Typically, PTSA can be in any solid state form. Preferably, PTSA is crystalline, more preferably, a hydrate, most preferably, a monohydrate.

Preferably, PTSA is added in an amount of about 0.5 mole equivalents to about 0.7 mole equivalents per mole equivalent of sorafenib base, more preferably about 0.5 mole equivalents per mole equivalent of sorafenib base, thus providing sorafenib hemi-tosylate.

Preferably, the addition of PTSA provides the solution comprising dissolved sorafenib hemi-tosylate, from which it is precipitated in crystalline form.

Preferably, precipitation is done by cooling the solution, providing the suspension. Preferably, cooling is to a temperature of about room temperature to about 0° C., more preferably to a temperature of about 15° C. to about 0° C.

The obtained suspension can be maintained to increase the yield of the precipitated crystalline form. Preferably, the suspension is maintained for about 2 hours to about 2 days, more preferably for about 1 day to about 2 days.

The process for preparing Sorafenib hemi-tosylate form A may further comprises recovering the crystalline form from the suspension, however, excluding drying by heating to a temperature greater than 100° C. The recovery may be done for example, by filtering, washing and drying. Preferably, the drying is done at a temperature of about 20° C. to about 70° C. Preferably drying is done to a period of about 30 minutes to about 5 hours. Optionally, drying is done by reduced pressure. Preferably the pressure is about 0.1 mBar to about 100 mBar, more preferably about 1 mBar to about 10 mBar. Preferably, when drying is done by reduced pressure, it is done over a period of about 30 minutes to about 5 hours.

In one embodiment, the invention encompasses the preparation of sorafenib tosylate from sorafenib hemi-tosylate. Preferably, the sorafenib hemi-tosylate is crystalline Sorafenib hemi-tosylate form A.

In another embodiment, the invention encompasses the preparation of sorafenib tosylate from sorafenib hemi-tosylate prepared according to the process of the present invention. Preferably, the sorafenib hemi-tosylate is crystalline Sorafenib hemi-tosylate form A.

Generally, preparing Sorafenib tosylate from Sorafenib hemi-tosylate comprises reacting Sorafenib hemi-tosylate and PTSA. Preferably, the reaction can be done, for example, by reacting PTSA and a mixture comprising Sorafenib hemi-tosylate and methanol.

In one embodiment, the invention encompasses a dimethyl sulfoxide ("DMSO") solvate of sorafenib tosylate.

Figure 2:
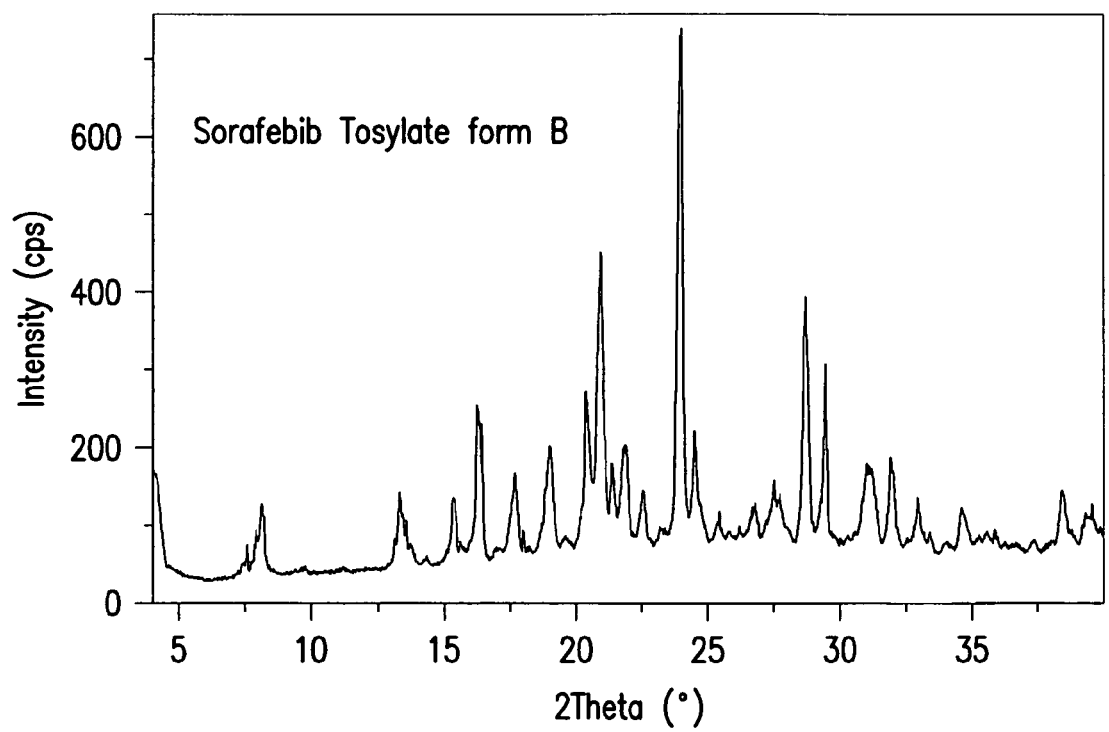
FIG. 2 shows a powder XRD pattern of crystalline Sorafenib tosylate Form B.
Figure 3:
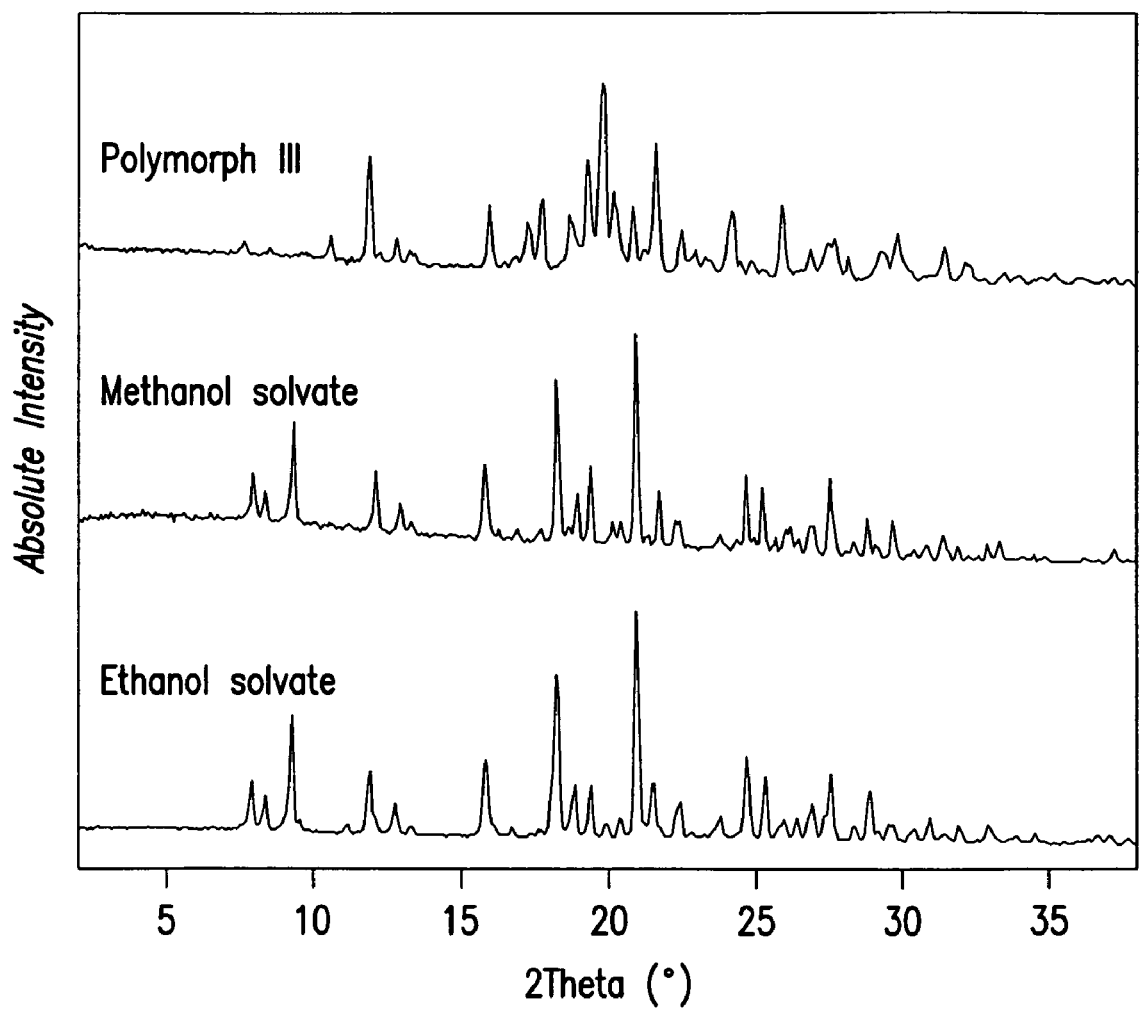
FIG. 3 shows powder XRD patterns of crystalline Sorafenib tosylate Form III, methanol solvate, and ethanol solvate.

In another embodiment, the invention encompasses the crystalline dimethylsulfoxide ("DMSO") solvate of Sorafenib tosylate characterized by a data selected from a group consisting of: A PXRD pattern having any 5 peaks selected from the list consisting of: 8.1, 15.3, 16.2, 17.7, 19.0, 20.4, 10.9, 21.8, 24.0, 24.5, 28.7 and 29.5±0.2 degrees 2theta; a PXRD pattern as depicted in FIG. 2 and combinations thereof. This form is designated form B.

Preferably, crystalline dimethylsulfoxide ("DMSO") solvate form B of Sorafenib tosylate is characterized by a PXRD pattern having 3 peaks at about 8.1, 15.3 and 24.0±0.2 degrees 2theta and 2 to 3 peaks selected from the list consisting of: 16.2, 17.7, 19.0, 21.8, 28.7 and 29.5±0.2 degrees 2theta.

Crystalline form B of sorafenib tosylate can be can be further characterized by data selected from the group consisting of: a PXRD pattern having peaks at about 8.1, 16.2, 17.7, 21.8, and 28.7±0.2 degrees 2-theta; a PXRD pattern having peaks at about 8.1, 16.2, 17.7, 21.8 and 24.0±0.2 degrees 2-theta; a PXRD pattern having peaks at about 8.1, 15.3, 16.2, 19.0, and 24.0±0.2 degrees 2-theta; and a PXRD pattern having peaks at about 8.1, 15.3, 21.8, 24.5 and 28.7±0.2 degrees 2-theta.

In addition, crystalline dimethylsulfoxide ("DMSO") solvate form B of Sorafenib tosylate has less than about 15% by weight, preferably, less than about 10% by weight, more preferably, less than about 5% by weight of crystalline Sorafenib tosylate selected from the group consisting of crystalline Sorafenib tosylate Polymorphs I, II and III. Typically, the amount of polymorph I in form B is measured by PXRD using any peak from the following list of peaks at about: 4.4, 11.1, 14.8, 16.7 and 22.9 deg±0.2 degrees 2-theta. Typically, the amount of polymorph II in form B is measured by PXRD using any peak from the following list of peaks at about: 8.8, 10.5, 12.4 and 12.8 deg±0.2 degrees 2-theta. Typically, the amount of polymorph III in form B is measured by PXRD using any peak from the following list of peaks at about: 10.7, 12.0, 19.9, and 25.9 deg±0.2 degrees 2-theta.

Crystalline dimethylsulfoxide ("DMSO") solvate of Sorafenib tosylate of Form B, can be prepared by a process comprising crystallizing sorafenib tosylate from DMSO.

Typically, the crystallization process comprises providing a solution of Sorafenib tosylate and DMSO and precipitating the crystalline form to obtain a suspension comprising the crystalline form.

Preferably, the solution is provided by combining sorafenib tosylate and DMSO.

Preferably, the precipitation comprises maintaining the solution at a temperature of about 20° C.

Preferably, the solution is maintained for a period of about 1 day to about 2 weeks, more preferably for a period of 2 weeks, providing the suspension The process for preparing crystalline form B of sorafenib tosylate can further comprise recovering the crystalline form from the suspension. The recovery can be done for example by filtering the suspension and drying at about room temperature.

In one embodiment, the invention encompasses N-methylpyrrolidone ("NMP") solvate of sorafenib tosylate.

Figure 6:
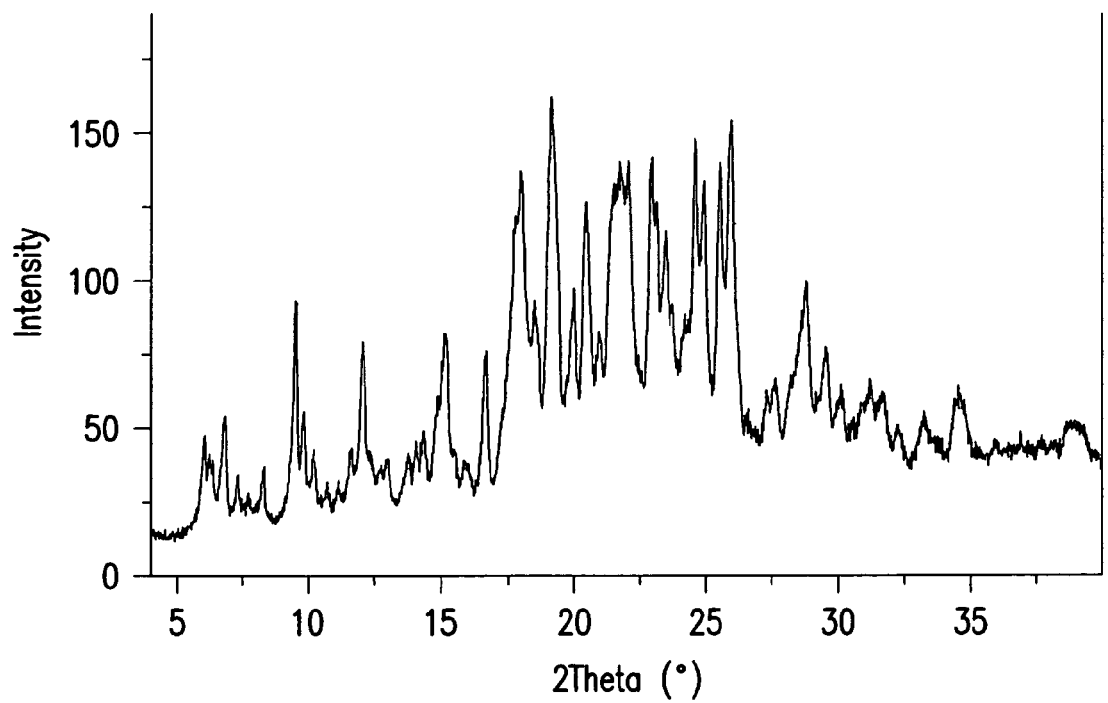
FIG. 6 shows a powder XRD pattern of crystalline Sorafenib tosylate Form C.

In another embodiment, the invention encompasses the crystalline N-methyl pyrrolidone ("NMP") solvate of Sorafenib tosylate characterized by a data selected from a group consisting of: A PXRD pattern having diffraction peaks at about: 6.8, 9.5, 15.1, 19.1 and 24.6±0.2 degrees 2theta; a PXRD pattern depicted in FIG. 6; and combination thereof. This form can be designated form C.

In addition, N-methylpyrrolidone ("NMP") solvate, designated form C, can be further characterized by a PXRD pattern having diffraction peaks at about: 12.0, 16.7, 18.0, 20.4, 22.9 and 26.0±0.2 degrees 2theta.

The above form C can be prepared by a process comprising crystallizing Sorafenib tosylate from a mixture comprising NMP and TBME.

Preferably, the crystallization comprises dissolving Sorafenib tosylate in NMP to obtain a solution, and adding the solution to tert-butyl methyl ether ("TBME") while stirring to obtain a suspension.

Preferably, the addition is done drop wise, i.e., TBME is added gradually, over a period of about 30 minutes.

Typically, the suspension can be further maintained to increase the yield of the precipitated crystalline form. Preferably, the suspension can be maintained, preferably maintaining is for a period of about overnight.

The process for preparing crystalline form C of Sorafenib tosylate can further comprise recovering the crystalline form from the suspension. The recovery can be done for example by filtering the suspension, washing and drying at about room temperature. Preferably, washing is done with TBME.

The above forms of sorafenib hemi-tosylate or sorafenib tosylate can be used to prepare pharmaceutical compositions for the treatment of advanced renal cell carcinoma.

In one embodiment, the invention encompasses a pharmaceutical composition comprising sorafenib hemi-tosylate or at least one of the above-described polymorphs of sorafenib hemi-tosylate or sorafenib tosylate, and at least one pharmaceutically acceptable excipient.

In one embodiment, the present invention also encompasses a pharmaceutical composition comprising sorafenib hemi-tosylate or at least one of the above described polymorphs of sorafenib hemi-tosylate or sorafenib tosylate prepared according to the processes of the present invention, and at least one pharmaceutically acceptable excipient.

In another embodiment, the invention encompasses a process for preparing a pharmaceutical composition comprising sorafenib hemi-tosylate or at least one of the above polymorphs of sorafenib hemi-tosylate or sorafenib tosylate, and at least one pharmaceutically acceptable excipient.

In another embodiment, the invention encompasses a method of treating advanced renal cell carcinoma comprising administering a pharmaceutical composition comprising sorafenib hemi-tosylate or at least one of the above polymorphs of sorafenib hemi-tosylate or sorafenib tosylate to a patient in need thereof.

EXAMPLES

PXRD

PXRD diffraction was performed on X-Ray powder diffractometer: Philips X'pert Pro powder diffractometer, CuKα radiation, λ=1.541874 Å. X'Celerator detector active length (2theta)=2.122 mm, laboratory temperature 22-25° C. Zero background sample-holders.

Prior to analysis the samples were gently ground by means of mortar and pestle in order to obtain a fine powder. The ground sample was adjusted into a cavity of the sample holder and the surface of the sample was smoothed by means of a cover glass.

Solid-State NMR

All $^{13}$C CP/MAS NMR spectra were measured at 125 MHz using Bruker Avance 500 WB/US NMR spectrometer (Karlsruhe, Germany, 2003) at magic angle spinning (MAS) frequency ωr/2π=11 kHz. In all cases finely powdered samples were placed into the 4 mm ZrO2 rotors and standard CPMAS pulseprogram was used. During acquisition of the data a high-power dipolar decoupling TPPM (two-pulse phase-modulated) was applied. The phase modulation angle was 15°, and the flip-pulse length was 4.8 μs. Applied nutation frequency of B1(1H) field was ω1/2π=89.3 kHz. Nutation frequency of B1($^{13}$C) and B1(1H) fields during cross-polarization was ω1/2π=62.5 kHz and repetition delay was 4 s. The number of scans was about 4800 consequently the total experimental time was about 5 hours (to achieve acceptable S/N ratio). The $^{13}$C scale was calibrated with glycine as external standard (176.03 ppm—low-field carbonyl signal). Subsequently also $^{13}$C single-pulse NMR experiment with pulse-width 3 μμs and repetition delay 30 s was performed.

Example 1

Preparation of Sorafenib Base According to U.S. Pat. No. 7,235,576

A solution of 4-chloro-3-(trifluoromethyl)phenylisocyanate (14.60 g, 65.90 mmol) in CH2C12 (35 mL) was added dropwise to a suspension of 4-(2-(N-methylcarbamoyl)-4-pyridyloxy)aniline (MethodA2, Step 4; 16.0 g, 65.77 mmol) in CH2C12 (35 mL) at 0° C. The resulting mixture was stirred at room temp. for 22 h. The resulting yellow solids were removed by filtration, then washed with CH2C12 (2×30 mL) and dried under reduced pressure to afford N-(4-chloro-3-(trifluoromethyl)phenyl)-N'-(4-(2-(N-methylcarbamoyl)-4-pyridyloxy)phenyl) as an off white solid (28.5 g, 93%)

Example 2

Preparation of Sorafenib Tosylate Methanol Solvate

A solution of PTSA.H$_2$O (5 g, 26.2 mmol) in MeOH (15 g) was added under stirring to a suspension of Sorafenib base (10 g, 21.5 mmol) in MeOH (30 g) at room temperature. The mixture suspension was then cooled to 2-3° C. and kept under stirring at this temperature for 1 h. The solid was filtered off and washed on the filter with MeOH. Sorafenib tosylate methanol solvate was obtained (about 14.3 g).

Example 3

Preparation of Sorafenib Tosylate Methanol Solvate

A solution of PTSA.H$_2$O (12 g, 63 mmol) in MeOH (50 g) was added under stirring to a suspension of Sorafenib base (20 g, 43 mmol) in MeOH (200 g) at reflux. The solution was kept under stirring at reflux temperature for 30 min, then it was cooled to 30° C. and kept under stirring for 1.5 h. The solid was filtered off, washed on the filter with MeOH and dried at room temperature for 15 h. Sorafenib tosylate methanol solvate was obtained (about 28 g).

Example 4

Preparation of Sorafenib Tosylate Methanol Solvate

A solution of PTSA.$H_2O$ (8.25 g, 43.4 mmol) in MeOH (30 g) was added under stirring to a suspension of Sorafenib base (13.75 g, 29.6 mmol) in NMP (30 g) at room temperature. The solution was filtered and then additional MeOH (270 g) pre-cooled at 5° C. was added. The suspension was cooled to 2-3° C. and kept under stirring for 1 h. The solid was filtered off, washed on the filter with MeOH and dried at room temperature. Sorafenib tosylate methanol solvate was obtained (19.6 g).

Example 5

Preparation of Sorafenib Tosylate Methanol Solvate

PTSA.$H_2O$ (17 g) was added to a solution of Sorafenib tosylate polymorph I (260 g) in DMSO (380 g) and MeOH (195 g), at about room temperature. The solution was filtered and diluted with MeOH (3200 g) pre-cooled at 8° C. The mixture was cooled at 2-3° C. and stirred for 1 h. The solid was filtered off, washed on the filter with MeOH and dried at room temperature. Sorafenib tosylate methanol solvate was obtained (275 g).

Example 6

Preparation of Sorafenib Tosylate Polymorph III

Sorafenib tosylate methanol solvate (5 g) was dried at 80° C. under vacuum for 16 h furnishing Sorafenib tosylate polymorph III (4.7 g).

Example 7

Preparation of Sorafenib Tosylate Ethanol Solvate

Sorafenib tosylate polymorph III (10 g) was suspended in EtOH (50 g) and the mixture was stirred for 48 h at room temperature. The solid was filtered off, washed with EtOH and dried at room temperature for 16 h. Sorafenib tosylate ethanol solvate was obtained (10.4 g).

Example 8

Preparation of Crystalline Form A of Sorafenib Hemi-Tosylate

Sorafenib tosylate Form III (0.5 g) was suspended in water (20 ml) in a glass bottle. The bottle with suspension was placed in a laboratory ultrasound bath and ultrasound was applied for 1 h. During this time, the recrystallization of Form III to Form A took place and the suspension became more dense. Suspension was than cooled to 0.5° C. and stirred overnight facilitating the recrystallisation of small particles to larger crystals, which can be more easily filtered. Sorafenib hemi-tosylate Form A was recovered by filtration and dried in air.

Example 9

Preparation of Crystalline Form A of Sorafenib Hemi-Tosylate

Sorafenib base (450 mg) was dissolved in 2-propanol (20 ml) at 40° C. and cooled to 25° C. Toluenesulfonic acid monohydrate (225 mg in 0.6 ml of water) was added to the solution in one portion. The solution thus formed was cooled to 0.5° C. and allowed to crystallize for 2 days. Sorafenib hemi-tosylate Form A was recovered by filtration, washed with 2-propanol (10 ml) and dried in air.

Example 10

Preparation of Crystalline Form A of Sorafenib Hemi-Tosylate

Sorafenib base (450 mg) was dissolved in 1-propanol (6 ml) at 50° C. and cooled to 25° C. Toluenesulfonic acid monohydrate (225 mg in 0.6 ml of water) was added to the solution in one portion. The solution thus formed was allowed to crystallize at 15° C. for 1 day forming a dense suspension. Sorafenib hemi-tosylate Form A was recovered by filtration, washed with 1-propanol (10 ml) and t-butylmethylether (10 ml) and dried in air. The resulting material had the XRPD pattern shown in FIG. 1.

Example 11

Preparation of Sorafenib Hemi-Tosylate Form A

Sorafenib tosylate Form III (0.5 g) was suspended in water (20 ml) in a glass bottle. The bottle with suspension was placed in a laboratory ultrasound bath and ultrasound was applied for 1 h. During this time, the recrystallization of Form III to Form A took place and the suspension became more dense. Sorafenib tosylate Form A was recovered by filtration and dried in air.

Example 12

Preparation of Sorafenib Hemi-Tosylate Form A

Sorafenib base (450 mg) was dissolved in acetone (12 ml) at 30° C. Toluenesulfonic acid monohydrate (225 mg in 0.6 ml of water) was added to the solution in one portion. Crystallization was done at room temperature. Sorafenib hemi-tosylate Form A was recovered by filtration and dried on air at 25° C. for 2 h.

Example 13

Preparation of Crystalline Form B of Sorafenib Tosylate

Sorafenib tosylate 0.5 g was dissolved in DMSO (1 ml). Crystals were formed by standing at 20° C. for two weeks.

Then, the material was filtered and left to stand in air. The resulting material had the XRPD pattern shown in FIG. 2.

Example 14

Preparation of Sorafenib Tosylate Form C(N-methylpyrrolidone Solvate)

Sorafenib tosylate (Polymorph III, 300 mg) was dissolved in NMP (250 ul) and solution was added drop by drop to TBME (50 ml) under stirring. The mixture was allowed to crystallize overnight. Crystals were separated by filtration, washed with TBME (5 ml) and left to stand in air.

The invention claimed is:

1. A process for preparing crystalline Sorafenib tosylate characterized by a PXRD pattern having the peaks selected from the list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2 theta, said process comprising
a) combining Sorafenib tosylate, p-toluenesulfonic acid (PTSA) and a solvent selected from a group consisting of methanol, a mixture of methanol and N-methyl pyrrolidone (NMP), and a mixture of methanol and dimethylsulfoxide (DMSO), to obtain a suspension comprising Sorafenib tosylate methanol solvate;
b) recovering crystalline Sorafenib tosylate methanol solvate from the suspension; and
c) drying the crystalline Sorafenib tosylate methanol solvate at a temperature greater than room temperature to obtain crystalline Sorafenib tosylate.

2. The process of claim 1, wherein the suspension is obtained by combining Sorafenib base or Sorafenib tosylate and PTSA in a solvent selected from the group consisting of: methanol, mixtures of methanol and NMP, mixtures of DMSO and methanol, to obtain the suspension of Sorafenib tosylate methanol solvate, from which crystalline Sorafenib tosylate methanol solvate precipitates.

3. The process of claim 2, wherein a methanolic solution of PTSA reacts with a suspension of Sorafenib base in methanol.

4. The process of claim 2, wherein a methanolic solution of PTSA reacts with a suspension of Sorafenib base in NMP.

5. The process of claim 2, wherein PTSA reacts with a solution of Sorafenib tosylate in a mixture of methanol and DMSO to obtain a second solution of Sorafenib tosylate.

6. The process of claim 5, wherein the second solution is then combined with methanol providing the suspension comprising crystalline sorafenib tosylate methanol solvate.

7. The process of claim 1, wherein recovering of crystalline Sorafenib tosylate methanol solvate comprises drying at a temperature of less than about 30° C.

8. The process of claim 1, wherein the drying in step c) is done at a temperature of about 80° C. to about 90° C.

9. A process for preparing crystalline Sorafenib tosylate methanol solvate characterized by a PXRD pattern having the peaks selected from the list consisting of: 8.0, 8.4, 9.3, 11.2, 12.2, 13.0, 13.4, 15.8, 16.3, 16.9, 17.7, 18.3, 18.7, 19.0, 19.4, 20.2, 20.5, 20.9, 21.4, 21.7, 22.3, 22.4, 23.8, 24.0, 24.4, 24.7, 24.9, 25.2, 25.7, 26.0, 26.1, 26.4, 26.9, 27.0, 27.5, 27.7, 28.1, 28.3, 28.8, 29.1, 29.7, 30.2, 30.4, 30.7, 30.8, 31.4, 31.6, 31.9, 32.3, 32.6, 32.9, 33.4, 33.8, 34.0, 34.2, 34.5, 34.9, 36.2, 36.6, 37.2, and 37.7±0.2 degrees 2 theta; comprising combining Sorafenib tosylate, PTSA and a solvent selected from a group consisting of methanol, a mixture of methanol and NMP, and a mixture of methanol and DMSO, to obtain a suspension comprising crystalline Sorafenib tosylate methanol solvate.

10. A process for preparing crystalline Sorafenib tosylate ethanol solvate characterized by a PXRD pattern having the peaks selected from the list consisting of: 7.9, 8.4, 9.3, 9.5, 11.2, 12.0, 12.2, 12.8, 13.4, 15.9, 16.1, 16.8, 17.4, 17.7, 18.1, 18.3, 18.6, 18.8, 19.4, 20.0, 20.4, 21.0, 21.2, 21.5, 21.7, 22.3, 22.4, 22.8, 23.3, 23.6, 23.8, 24.3, 24.7, 25.3, 25.8, 25.9, 26.4, 26.9, 27.3, 27.6, 28.3, 28.8, 29.1, 29.5, 29.7, 30.2, 30.4, 30.9, 31.4, 32.0, 32.6, 32.9, 33.2, 33.7, 33.9, 34.5, 35.5, 36.0, 36.3, 36.6, 37.1, and 37.7±0.2 degrees 2theta; comprising suspending sorafenib tosylate characterized by a PXRD pattern having the peaks selected from the list consisting of: 7.7, 8.5, 9.8, 10.6, 12.0, 12.3, 12.9, 13.4, 13.5, 15.4 and 16.0, 16.5, 16.9, 17.3, 17.8, 18.7, 18.8, 19.3, 19.9, 20.3, 20.8, 21.2, 21.6, 22.5, 23.0, 23.4, 24.2, 24.5, 24.8, 25.2, 25.9, 26.9, 27.5, 27.7, 28.2, 29.2, 29.4, 29.8, 30.3, 31.4, 32.2, 33.5, 34.0, 35.2, 36.1, 37.2, and 37.7±0.2 degrees 2 theta, in ethanol.

11. The process of claim 10, wherein the suspension is prepared at a temperature of about 15° C. to about 30° C.

12. The process of claim 10, wherein the obtained crystalline sorafenib tosylate ethanol solvate is recovered from the suspension.

13. The process of claim 12, wherein the recovery includes drying is done at a temperature of less than about 30° C.

* * * * *